US007074755B2

(12) United States Patent
Heavner

(10) Patent No.: US 7,074,755 B2
(45) Date of Patent: Jul. 11, 2006

(54) ERYTHROPOIETIN CONJUGATE COMPOUNDS WITH EXTENDED HALF-LIVES

(75) Inventor: George Heavner, Malvern, PA (US)

(73) Assignee: Centocor, Inc., Malvern, PA (US)

( * ) Notice: Subject to any disclaimer, the term of this patent is extended or adjusted under 35 U.S.C. 154(b) by 127 days.

(21) Appl. No.: 10/439,870

(22) Filed: May 17, 2003

(65) Prior Publication Data

US 2004/0229318 A1    Nov. 18, 2004

(51) Int. Cl.
*A61K 38/00* (2006.01)
*C07K 1/00* (2006.01)
*C07K 14/00* (2006.01)

(52) U.S. Cl. .......................... 514/2; 530/402; 530/345; 530/350

(58) Field of Classification Search .................... 514/2; 530/402, 345, 350
See application file for complete search history.

(56) References Cited

U.S. PATENT DOCUMENTS

| 5,438,040 | A | 8/1995 | Ekwuribe | 514/3 |
| 6,025,324 | A | 2/2000 | Bailon et al. | 530/351 |
| 6,077,939 | A | 6/2000 | Wei et al. | 530/402 |
| 6,180,134 | B1 * | 1/2001 | Zalipsky et al. | 424/450 |
| 6,340,742 | B1 | 1/2002 | Burg et al. | 530/351 |
| 6,465,694 | B1 * | 10/2002 | Baudys et al. | 568/494 |

FOREIGN PATENT DOCUMENTS

| EP | 0 539 167 A2 | 10/1992 |
| EP | 0 605 963 A2 | 12/1993 |
| WO | WO 94/28024 A1 | 12/1994 |
| WO | WO 00/26256 A2 | 5/2000 |
| WO | WO 01/02017 A2 | 1/2001 |

OTHER PUBLICATIONS

Zalipsky et al. Peptide Attachment to Extremities of Liposomal Surface Grafted PEG Chains: Preparatoin of the Long-Circulating Form of Laminin Pentapeptide, YIGSR. 1995, Bioconjugate Chem. 6: 705-708.*
Allen et al. A new Strategy for attachment of antibodies to sterically stabilized liposomes resulting in efficient targeting to cancer cells. 1995, Biochim. Biophys. Acta 1237: 99-108.*
McKenzie, Shrirlyn B. Textbook of Hematology, 1996, William & Wilkins, Baltimore, MD, p. 40.*

* cited by examiner

*Primary Examiner*—Nashaat T. Nashed
*Assistant Examiner*—Holly Schnizer
(74) *Attorney, Agent, or Firm*—Kenneth J. Dow

(57) ABSTRACT

The invention provides biologically active erythropoietin (EPO) conjugate compositions wherein EPO is covalently conjugated to a non-antigenic hydrophilic polymer covalently linked to an organic molecule that increases the circulating serum half-life of the composition. The invention thus relates to EPO derivatives described by the formula EPO-$(X-Y)_N$ where EPO is erythropoietin or its pharmaceutical acceptable derivatives having biological properties of causing bone marrow cells to increase production of reticulocytes and red blood cells, X is PEG or other water soluble polymers, Y is an organic molecule that increases the circulating half-life of the construct more than the PEG alone and N is an integer from 1 to 15. Other molecules may be included between EPO and X and between X and Y to provide the proper functionality for coupling or valency.

18 Claims, 2 Drawing Sheets

ERYTHROPOIETIN CONJUGATE COMPOUNDS WITH EXTENDED HALF-LIVES

FIELD OF THE INVENTION

The present invention relates to novel formulations of erythropoietin. In particular, the invention relates erythropoietin conjugate compounds having extended half-lives.

BACKGROUND OF THE INVENTION

Erythropoietin (EPO) is a glycoprotein and a colony stimulating factor which serves as the principal factor involved in the regulation of red blood cell synthesis. Erythropoietin is produced in the kidney and acts by stimulating precursor cells in bone marrow causing them to divide and differentiate into mature red blood cells. Naturally occurring EPO is a glycoprotein containing 165 amino acids that is produced in the kidney. Erythropoietin has been manufactured using recombinant DNA technology through the cloning of the EPO gene and expression in Chinese hamster ovary cells. See Lin, U.S. Pat. No. 5,618,698. The recombinantly produced EPO has been available for some time as an effective therapeutic agent in the treatment of various forms of anemia, including anemia associated with chronic renal failure, zidovidine treated HIV infected patients, and cancer patients on chemotherapy. The glycoprotein is administered parenterally, either as an intravenous (IV) or subcutaneous (SC) injection in conventional buffered aqueous solutions which contain human serum albumin (HSA) as a carrier. Such formulations are marketed in the United States under the trade names EPOGEN® and PROCRIT®. These products contain erythropoietin in 1 ml single dose, preservative-free or 2 ml multidose preserved vials.

While these formulations have been proven to be highly successful, certain disadvantages are associated with the products. Presently, the bioavailability of protein therapeutics such as erythropoietin is limited by short plasma half-lives and the susceptibility to protease degradation. The short half-lives of proteins such as erythropoietin necessitate frequent administration for maximum clinical efficacy. This is disadvantageous for the treatment of chronic conditions and can results in poor patient compliance, reducing efficacy. Accordingly, attempts have been made to increase the plasma half-life of erythropoietin.

In recent years, non-antigenic water-soluble polymers, such as polyethylene glycol ("PEG") have been used for the covalent modification of polypeptides of therapeutic and diagnostic importance. For example, covalent attachment of PEG to therapeutic polypeptides such as the interleukins (Knauf, M. J. et al., *J. Biol. Chem.* 1988, 263, 15,064; Tsutsumi, Y. et al., *J. Controlled Release* 1995, 33, 447), interferons (Kita, Y. et al., *Drug Des Delivery* 1990, 6, 157), catalase (Abuchowski, A. et al., *J. Biol Chem.* 1977, 252, 3, 582), superoxide dismutase (Beauchamp, C. O. et al., *Anal Biochem.* 1983, 131, 25), and adenosine deaminase (Chen, R. et al, *Biochim, Biophy. Acta* 1981, 660, 293), has been reported to extend their half-life in vivo, and/or reduce their immunogenicity and antigenicity.

Derivatized PEG compounds have been previously disclosed (U.S. Pat. No. 5,438,040, Aug. 1, 1995, Conjugation-Stabilized Polypeptide Compositions, Therapeutic Delivery and Diagnostic Formulations Comprising Same, and Method of Making and Using the Same, N. N. Ekwuribe). This approach to post-translational derivatization has also been applied to erythropoietin (EPO). For example, WO 94/28024 discloses carbohydrate modified polymer conjugates with erythropoietin activity wherein the PEG is linked via an oxidized carbohydrate. U.S. Pat. No. 4,904,584 discloses polyalkylene oxide conjugation of lysine-depleted polypeptide variants, including EPO. WO 90/12874 describes the preparation of a monomethoxy-PEG-EPO (mPEG-EPO) in which the EPO contains a cysteine residue introduced by genetic engineering to which the specific PEG reagent is covalently attached. Other PEG-EPO compositions are disclosed in EP 605693, U.S. Pat. No. 6,077,939, WO 01/02017 and EP 539167.

Applicant's co-pending application Ser. No. 09/431,861 discloses the modification of antibodies and antibody fragments with PEG and demonstrates that PEG can increase circulating half-life in mice and primates. Derivatized PEG was used for modification of the Fab fragment of the antibody c7E3. Circulating half-life is increased in direct proportion to the molecular weight of the PEG. As the molecular weight of PEG increases, the activity of the compound to inhibit ADP-induced platelet aggregation in vitro is decreased, while the binding to purified GPIIb/IIIa, as measured by BIAcore, is unaffected. The addition of a fatty acid or a lipid to the PEG ($PEG_{3.4K}$-DSPE [disteroylphosphatidylethanolamine]) had a greater circulating half-life than did $PEG_{5K}$. While there is a decrease in the in vitro activity of c7E3 Fab'$(PEG_{5k})_2$ relative to c7E3 Fab, the activity of c7E3 Fab'-$(PEG_{3.4K}$-DSPE$)_2$ is equivalent to c7E3 Fab.

SUMMARY OF THE INVENTION

Figure 1:
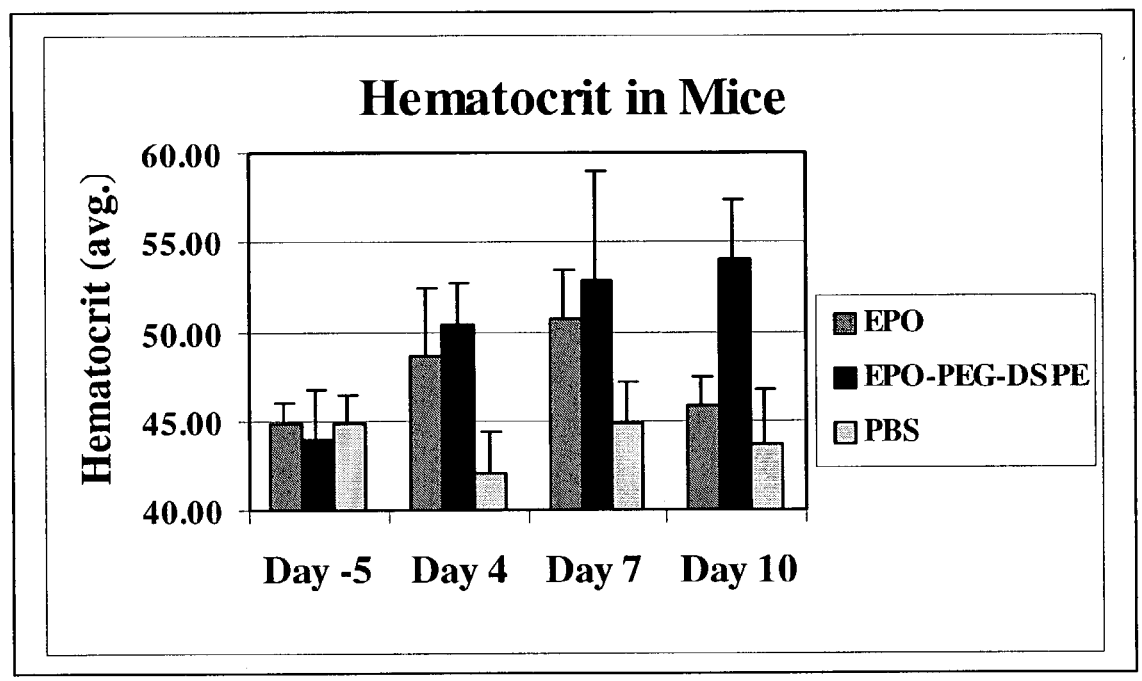
FIG. 1 is a graph showing the hematoctit in mice treated with the composition of the invention versus unmodified EPO and PBS control.

The invention provides biologically active EPO conjugate compositions wherein EPO is erythropoietin or its pharmaceutical acceptable derivatives having biological properties of causing bone marrow cells to increase production of reticulocytes and red blood cells, wherein the EPO is covalently conjugated to a non-antigenic hydrophilic polymer covalently linked to an organic molecule that increases the circulating serum half-life of the composition.

The invention thus relates to EPO derivatives described by the formula EPO-$(X-Y)_N$ where EPO is erythropoietin or its pharmaceutical acceptable derivatives having biological properties of causing bone marrow cells to increase production of reticulocytes and red blood cells, X is PEG or other water soluble polymers, Y is an organic molecule that increases the circulating half-life of the construct more than the PEG alone and N is an integer from 1 to 15. Other molecules may be included between EPO and X and between X and Y to provide the proper functionality for coupling or valency.

Erythropoietin (EPO) has a relatively short half-life (4–6 hours). There is thus a continuing need for EPO formulations having an increased half-life but which maintain the activity of the EPO molecule. The addition of PEG chains or other hydrophilic polymers with terminal modifications or other functionalities, (e.g. PPG or polyamide chains) (side chain functionality with or without terminal functionality) results in increases in circulating half-lives larger than those obtained with PEG alone.

Preferably, the active ingredient is erythropoietin or its derivatives having the biological properties of causing bone marrow cells to increase production of reticulocytes and red blood cells. The EPO glycoprotein may be obtained from natural sources or produced recombinantly using known procedures as disclosed in U.S. Pat. Nos. 4,703,008, 5,441,868, 5,547,933, 5,618,698 and 5,621,080, hereby incorporated by reference.

The organic molecule is covalently attached to the hydrophilic polymer and is selected from an organic moiety that is capable of increasing the in vivo half-life of the resulting construct. The hydrophilic polymer is preferably a polyalkylene oxide such as polyethylene glycol.

The present invention also provides methods of preparing the conjugates. The methods include the step of reacting a protein or glycoprotein having erythropoietic activity with a substantially non-antigenic functionalized hydrophilic polymer having a linking group for attaching the polymer to the glycoprotein. Preparation methods include reacting EPO with an activated form of a polyalkylene oxide that will react with a functional group on EPO. This includes activated polyalkylene oxides such as active esters, hydrazide, hydrazine, semicarbazide, thiosemicarbazide maleimide or haloacetyl polyalkylene oxide.

The invention also provides methods of treating anemia or other conditions associated with reduced endogenous erythropoietin or erythropoiesis or conditions under which an increase in red cells is desired. In this aspect of the invention, treatment includes administering an effective amount of the conjugates described herein to mammals requiring such therapy.

As a result of the present invention, conjugates having substantially prolonged erythropoietic activity in vivo are provided. These high activity conjugates are substantially resistant to in vivo hydrolysis, and thus require less frequent administration and often lower dosages when compared to unmodified EPO.

Advantages of the techniques discloses herein are increased half-life of EPO over simple PEGylation, increased half-life using lower molecular weight PEG, increased half-life by specific, in vivo binding of the functional moiety and less frequent dosing than for native EPO.

DETAILED DESCRIPTION

The active ingredient used in the present invention is erythropoietin and its derivatives having the biological properties of causing bone marrow cells to increase production of reticulocytes and red blood cells. The EPO formulations of the present invention are useful as a parenteral formulation in treating blood disorders characterized by low or defective red blood cell production such as various forms of anemia, including anemia associated with chronic renal failure, zidovidine treated HIV infected patients, and cancer patients on chemotherapy. It may also have application in the treatment of a variety of disease states, disorders and states of hematologic irregularity such as sickle cell disease, beta-thalassemia, cystic fibrosis, pregnancy and menstrual disorders, early anemia of prematurity, spinal cord injury, space flight, acute blood loss, aging and the like. It may also have application in situations where an increase in red blood cells is desired such as in pre-surgery patients. Preferably, the EPO composition of the present invention is administered parenterally (e.g. IV, IM, SC or IP). Effective dosages are expected to vary considerably depending on the condition being treated and the route of administration but are expected to be in the range of 0.1 (~7 U) to 100 (~7000 U) μg/kg body weight of the active material. Preferable doses for treatment of anemic conditions are about 50 to about 300 Units/kg three times a week.

The non-antigenic water-soluble polymers in the conjugates include polyalkylene oxides, polyvinyl pyrrolidone, homo-polyamino acids, hetero-polyamino acids, polyamides and carbohydrates. Within this group of substances are alpha-substituted polyalkylene oxide derivatives such as polypropylene glycol or other suitable alkyl-substituted derivatives such as $C_1$–$C_6$ groups. Non-antigenic polymer PEG homopolymer are suitable. Alternative polyalkylene oxides such as other polyethylene glycol homopolymers, polypropylene glycol homopolymers, other alkyl-polyethylene oxides, bis-polyethylene oxides and co-polymers or blocked co-polymers of polyalkylene oxides are also useful. The polymers may be either linear or branched.

The polymers must contain a functionality that can be covalently attached to EPO, a chemically enzymatically modified EPO or similar erythropoietic moiety. They must contain additional functionality that can be used to attach one or more organic moieties having properties that increase the in vivo half-life of the resulting construct.

Attachment of the functionalized, water-soluble polymer can be by non-site specific means, under conditions that do not adversely affect the activity of EPO, although site-specific attachment is preferred. Examples of methods of attachment include, but are not limited to:

1. Glyoxyl modification of the N-terminal amino group followed by reductive alkylation with an amine, hydrazine, oxime, semicarbazide or other appropriate nucleophile.
2. Periodic acid oxidation of one or more carbohydrates on EPO followed by reductive alkylation with an amine, hydrazine, oxime, semicarbazide or other appropriate nucleophile.
3. Reverse proteolysis to attach an organic moiety containing a nucleophile to the C- or N-terminal of EPO, followed by reductive alkylation or reaction with a suitable electrophile.
4. Production of EPO containing one or more additional cysteines, followed by its reaction with a suitable maleimide to form a thioether or activated thiol to form a disulfide, or halo compound to form a thioether.
5. Reaction of an active ester with amino groups on EPO either nonspecifically or site-specifically using pH, steric, stochiometric or kinetic control.

Further examples of the types of chemistry that may be employed are found in Techniques in Protein Modification by Roger L. Lundblad, CRC Press, 1995.

A specific example of N-terminal derivatization of EPO with an unfunctionalized PEG is taught by Wei, et al., U.S. Pat. No. 6,077,939, Jun. 20, 2000.

In those aspects of the invention in which PEG-based polymers are used, it is preferred that they have average molecular weights between about 200 and about 100,000 daltons, and preferably between about 2,000 and about 20,000 daltons. A molecular weight of 2,000 to 5,000 daltons is most preferred.

Alternative non-antigenic polymeric substances include materials such as dextrans, polyvinyl pyrrolidones, polysaccaharides, starches, polyvinyl alcohols, polyacrylamides or other similar non-immunogenic polymers. Those of ordinary skill in the art realize that the foregoing is merely illustrative and unintended to restrict the type of non-antigenic polymers suitable for use herein.

The functionalized polymers can be homo or heterobifunctional. Thus, the artisan can prepare cross-linked EPO conjugates or three-part conjugates containing EPO, a functionalized polymer and an additional substance that enhances bioactivity. Such substances include interleukins such as IL-3 or IL-6, growth factors, stimulating factors such as CSF, GM-CSF, and the like, or peptides or other moieties known in the art to enhance the activity of glycopolypeptides in vivo.

The organic moieties that can be attached to the hydrophilic polymer to increase the half-life include fatty acids, dicarboxylic acids, monoesters or monoamides of dicarboxylic acids, lipids containing saturated fatty acids, lipids containing unsaturated fatty acids, lipids containing mixtures of saturated and unsaturated fatty acids, simple carbohydrates, complex carbohydrates, carbocycles (such as steroids), heterocycles (such as alkaloids), amino acid chains, proteins, enzymes, enzyme cofactors, or vitamins.

In one embodiment, the hydrophilic polymeric group is substituted with one to about six alkyl, fatty acid, fatty acid ester, lipid or phospholipid groups (as described herein, e.g., Formulas I and II). Preferably, the substituted hydrophilic polymeric group is a linear or branched PEG. Preferably, the substituted hydrophilic polymeric group is a linear PEG (e.g., PEG diamine) that is terminally substituted with a fatty acid, fatty acid ester, lipid or phospholipid group. Hydrophilic polymers that are substituted with an alkyl, fatty acid, fatty acid ester, lipid or phospholipid groups group can be prepared using suitable methods. For example, a modifying agent can be prepared by reacting monoprotected PEG diamine with an activated fatty acid (e.g., palmitoyl chloride). The resulting product can be deprotected, a suitable activating group can be introduced (e.g. maleimido), and the resulting modifying agent can be used to produce a modified EPO that comprises a PEG that is terminally substituted with a fatty acid group. A variety of other suitable synthetic schemes can be used. For example, a polymer comprising an amine group can be coupled to a carboxylate of the fatty acid or fatty acid ester as described herein, and an activated carboxylate (e.g. activated with N,N'-carbonyl diimidazole) on a fatty acid or fatty acid ester can be coupled to an hydroxyl group on a polymer.

Fatty acids and fatty acid esters suitable for modifying EPO of the invention can be saturated or can contain one or more units of unsaturation. In a preferred embodiment, the fatty acids and fatty acid esters comprise from about six to about forty carbon atoms or about eight to about forty carbon atoms. Fatty acids which are suitable for modifying antibodies of the invention includes, for example, n-dodecanoate ($C_{12}$, laurate), n-tetradecanoate ($C_{14}$, myristate), n-hexadecanoate ($C_{16}$, palmitate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta^9$-octadecanoate ($C_{18}$, oleate), all cis $\Delta^{5,8,11,14}$-eicosatetraenoate ($C_{20}$, arachidonate), octanedioic acid, tetradecanedioic acid, octadecandeioic acid, docosanedioic acid, and the like. Suitable fatty acid esters include monoesters of dicarboxylic acids which comprise a linear or branched lower alkyl group. The lower alkyl group can comprise from one to above twelve, preferably one to about six, carbon atoms. Suitable fatty acid esters for modifying antibodies of the invention include, for example, methyl octadecanoate, ethyl octadecanoate, propyl octadecanoate, butyl dodecanoate, sec-butyl dodecanoate, tert-butyl dodecanoate, neopentyl tetradecanoate, hexyl tetradecanoate, methyl cis-$\Delta^9$-octadecanoate, and the like.

The modification of EPO as described herein below is preferably performed using one or more modifying agents. A "Modifying agent" as the term is used herein, refers to the hydrophilic polymer, and organic molecule conjugate complex which comprises an activating group. An "Activating group" is a chemical moiety or functional group that can, under appropriate conditions, react with a second chemical group thereby forming a covalent bond between the modifying agent and a chemical group on the EPO molecule. For example, amine-reactive activating groups include electrophilic groups such as tosylate, mesylate, halo (chloro, bromo, iodo), N-hydroxysuccinimidyl esters (NHS), substituted phenyl esters, acyl halides and the like. Activating groups which can react with thiols include, for example, maleimide, iodoacetyl, acrylolyl, pyridyl disulfides, 5-thiol-2-nitrobenzoic acid thiol (TNB-thiol), and the like. An aldehyde or ketone functional group can be coupled to amine- or hydrazide containing molecules and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996). An activating group can be bonded directly to the hydrophilic polymer, conjugate complex or through a linker moiety, for example a $C_1$–$C_{12}$ hydrocarbyl group. As used herein, "hydrocarbyl group" refers to a hydrocarbon chain wherein one or more carbon atoms are optionally replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH—NH—.

Modifying agents which comprise a linker moiety can be produced, for example, by reacting a mono-Boc-alkyldiamine (e.g. mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoracetic acid (TFA) to expose a primary amine which can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference).

The modified EPO of the invention can be produced by reacting the EPO or EPO derivation molecule with a modifying agent, as described herein. In one embodiment, the modified EPO can be bound in a non-site specific manner by employing an amine-reactive modifying agent, for example, an NHS ester of a modified PEG. In another embodiment, the modified EPO can be bound in a site-specific manner by employing pH control to limit reactivity with an NHS ester of a modified PEG to the alpha amino group of the first amino acid. Thus, in one embodiment, the modified EPO can be produced by reacting EPO with one or more modifying agents to produce a modified EPO comprising one to about 8 organic moieties which are bonded to specific sites on the EPO molecule, for example a synthetically introduced (i.e., one more) cysteinyl residue. In particularly preferred embodiments, the modified EPO can comprise one or two linear PEG moieties of greater than 2,000 Daltons which are bonded to specific sites (e.g., one or more synthetically introduced cysteinyl residue) followed by reaction with a suitable maleimide to form a thioether or activated thiol to form a disulfide or a halo compound to form a thioether. For example, the modified EPO can be reacted with a thiol-reactive modifying agent, for example, O-(2-maleimidoethyl)-O'-steroyl-polyethylene glycol 5,000 to produce the modified EPO of the invention.

In another example, the modified EPO is produced by reverse proteolysis to attach an organic moiety containing a nucleophile to the carboxyl or amino terminal EPO followed by reductive alkylation or reaction with a suitable electrophile.

One method for preparing a modified erythropoietin is to introduce a unique functionality at the carboxyl or amino terminus of the EPO molecule through reverse proteolysis. "Reverse proteolysis" is a term of the art which refers to the fact that under particular conditions certain proteases can catalyze the formation of amide or ester bonds. For example, a purified EPO can be mixed with a protease and carbohydrazide under conditions suitable for reverse proteolysis (e.g., 250-fold molar excess of the carbohydrazide relative to the EPO), to produce an EPO molecule comprising a unique hydrazide function at the carboxyl terminus.

The hydrazide-containing EPO can be modified by reaction with a suitable modifying agent. For example, the EPO derivative can be reacted with a modifying agent comprising a carbonyl functional group to produce a modified EPO comprising an organic moiety that is specifically attached to the carboxyl terminus through a hydrazone-linkage. The hydrazone can be further stabilized by reaction with a suitable reducing agent (e.g. sodium cyanoborohydride).

Various enzymes can be used to introduce a hydrazide function by reverse proteolysis. The conditions for reverse proteolysis are known to those skilled in the art and include a large (e.g., 250-fold) molar excess of carbohydrazide and an extended reaction time. Additionally, the reverse proteolysis reaction may preferentially occur at a pH different from the optimal pH for proteolysis (Fisch et al., *Bioconjugate Chem.*, 3:147–153 (1992); Werlen et al., *Bioconjugate Chem.*, 5:411–417 (1994); Kumaran et al., *Protein Sci.* 6 (10): 2233–2241 (1997); Itoh et al., *Bioorg. Chem.*, 24(1): 59–68 (1996); Capellas et al., *Biotechnol. Bioeng.*, 56(4): 456–463 (1997). The optimal pH for reverse proteolysis can be determined empirically using standard methods. A preferred enzyme for carboxyl terminus modification is achromopeptidase.

Some examples of compounds are shown below. Although DSPE is used as the lipid in some of these examples, other lipids and phospholipids are included by analogy. Molecular weights of PEG are generally less than 30,000 and include linear, branched and star PEGs. PEG can also be replaced by other water-soluble polymers.

Examples of EPO derivatives include DSPE-PEG-EPO where the PEG-DSPE is joined to the N-terminus of EPO and EPO-(PEG-DSPE)$_2$ where two PEG-DSPE groups are joined with a valency-enhancing construct to the derivatized N-termini of EPO. Higher multiples are included as well. Valency enhancing construct are defined as a moiety containing at least three functional groups such that one functional group is used for attachment to an erythropoietic compound and the remaining functional groups are used for the attachment of two or more derivatized hydrophilic polymer constructs. The N terminal may be derivatized by glyoxyl modification. The glyoxyl group can be reacted with a hydrazine-derivatized hydrophilic polymer construct such as hydrazine-PEG-DSPE.

Examples of derivatized erythropoietic compounds are M-PEG-EPO where the M-PEG is attached non-specifically to lysine amino groups using a variety of different chemistries where M is a lipid, carbohydrate, polysaccharide, fatty acid, fatty acid derivative, fatty alcohol or protein.

(M-PEG)$_2$-EPO where the M-PEG is attached to two amino groups using a variety of different chemistries where M is a lipid, carbohydrate, polysaccharide, fatty acid, fatty acid derivative, fatty alcohol or protein. Higher multiples are included as well.

(M-PEG)$_2$-EPO where the (M-PEG)$_2$-R is attached to an amino group using a variety of different chemistries where M is a lipid, carbohydrate, polysaccharide, fatty acid, fatty acid derivative, fatty alcohol or protein and R is a valency enhancing construct. Higher multiples are included as well.

M-PEG-EPO where the M-PEG is attached to a cysteine in EPO created by the addition of an amino acid, the mutation of an existing amino acid or the addition of a thiol to EPO using a bifunctional agent and where M is a lipid, carbohydrate, polysaccharide, fatty acid, fatty acid derivative, fatty alcohol or protein.

(M-PEG)$_2$-EPO where the M-PEG is attached to two cysteines in EPO created by the addition of one or more amino acids, the mutation of existing amino acids, the addition of a thiol to EPO using a bifunctional agent or a combination of these and M is a lipid, carbohydrate, polysaccharide, fatty acid, fatty acid derivative, fatty alcohol or protein. Higher multiples are included as well.

(M-PEG)$_2$-EPO where the (M-PEG)$_2$-R is attached to a cysteine in EPO created by the addition of an amino acid, the mutation of an existing amino acid or the addition of a thiol to EPO using a bifunctional agent and M is a lipid, carbohydrate, polysaccharide, fatty acid, fatty acid derivative, fatty alcohol or protein and R is a valency enhancing construct. Higher multiples are included as well.

M-PEG-EPO where the M-PEG is attached by reductive alkylation to a carbonyl generated by the partial oxidation of a carbohydrate on EPO or by the addition of a carbonyl function by derivatization and M is a lipid, carbohydrate, polysaccharide, fatty acid, fatty acid derivative, fatty alcohol or protein.

(M-PEG)$_2$-EPO where the M-PEG is attached by reductive alkylation to two carbonyls generated by the partial oxidation of carbohydrates on EPO or by the addition of carbonyl functions by derivatization or a combination of these. Higher multiples are included as well.

(M-PEG)$_2$-EPO where the (M-PEG)$_2$-R is attached by reductive alkylation to two carbonyls generated by the partial oxidation of carbohydrates on EPO or by the addition of carbonyl functions by derivatizion or a combination of these and M is a lipid, carbohydrate, polysaccharide, fatty acid, fatty acid derivative, fatty alcohol or protein and R is a valency enhancing construct. Higher multiples are included as well.

M-PEG-EPO where the M-PEG is attached to an arginine guanidino group using a variety of different chemistries.

(M-PEG)$_2$-EPO where the M-PEG is attached to two arginine guanidino groups using a variety of different chemistries and M is a lipid, carbohydrate, polysaccharide, fatty acid, fatty acid derivative, fatty alcohol or protein. Higher multiples are included as well.

(M-PEG)$_2$-EPO where the (M-PEG)$_2$-R is attached to an arginine guanidino group using a variety of different chemistries where M is a lipid, carbohydrate, polysaccharide, fatty acid, fatty acid derivative, fatty alcohol or protein and R is a valency enhancing construct. Higher multiples are included as well.

M-PEG-EPO where the M-PEG is attached by reductive alkylation to a hydrazine (—NH—NH$_2$) generated by reverse proteolysis on the N- or C-terminal amino acids of EPO or by derivatization and M is a lipid, carbohydrate, polysaccharide, fatty acid, fatty acid derivative, fatty alcohol or protein.

(M-PEG)$_2$-EPO where the (M-PEG)$_2$-R is attached by reductive alkylation to two hydrazines (—NH—NH$_2$) generated by reverse proteolysis on the N- or C-terminal amino acids of EPO or by derivatization where M is a lipid, carbohydrate, polysaccharide, fatty acid, fatty acid derivative, fatty alcohol or protein. Higher multiples are included as well.

(M-PEG)$_2$-EPO where the (M-PEG)$_2$-R is attached by reductive alkylation to a hydrazine (—NH—NH$_2$) generated by reverse proteolysis on the N- or C-terminal amino acids of EPO or by derivatization where M is a lipid, carbohydrate, polysaccharide, fatty acid, fatty acid derivative, fatty alcohol or protein and R is a valency enhancing construct. Higher multiples are included as well.

Pharmaceutical Compositions

The erythropoietin glycoprotein products prepared in accordance with this invention may be prepared in pharmaceutical compositions suitable for injection with a pharmaceutically acceptable carrier or vehicle by methods known in the art. For example, appropriate compositions have been described in WO97/09996, WO97/40850, WO98/58660, AND wo99/07401. Among the preferred pharmaceutically acceptable carriers for formulating the products of the invention are human serum albumin, human plasma proteins, etc. The compounds of the present invention may be formulated in 10 mM sodium/potassium phosphate buffer at pH 7 containing a tonicity agent, e.g. 132 mM sodium chloride. Optionally the pharmaceutical composition may contain a preservative. The pharmaceutical composition may contain different amounts of erythropoietin products, e.g. 10–2000 µg/ml, e.g. 50 µg or 400 µg.

The stability of the composition can be further enhanced by the addition of antioxidants such as tocopherol, butylated hydroxytoluene, butylated hydroxyanisole, ascorbyl palmitate, or edetates such as e.g. disodium edetate, with the edetates additionally binding possibly present heavy metals. The stability can furthermore be enhanced by the addition of preserving agents such as benzoic acid and parabens, e.g. methylparaben, and/or propylparabene.

Treating Blood Disorders Characterized by Low or Defective Red Blood Cell Production Administration of the erythropoietin glycoprotein products of the present invention results in red blood cell formation in humans. Therefore, administration of the erythropoietin glycoprotein products replenishes this EPO protein which is important in the production of red blood cells. The pharmaceutical compositions containing the erythropoietin glycoprotein products may be formulated at a strength effective for administration by various means to a human patient experiencing blood disorders characterized by low or defective red blood cell production, either alone or as part condition or disease. The pharmaceutical compositions may be administered by injection such as by subcutaneous, intravenous or intramuscular injection. Average quantities of the erythropoietin glycoprotein product may vary and in particular should be based upon the recommendations and prescription of a qualified physician. The exact amount of conjugate is a matter of preference subject to such factors as the exact type of condition being treated, the condition of the patient being treated, as well as the other ingredients in the composition. For example, 0.01 to 10 µg per kg body weight, preferably 0.1 to 10 µg per kg body weight, may be administered e.g. once weekly.

Throughout this application, various publications have been referenced. The disclosures in these publications are incorporated herein by reference in order to describe more fully the state of the art.

The present invention is further illustrated by the following examples that are presented for purposes of demonstrating, but not limiting, the preparation of the compounds and compositions of this invention.

EXAMPLE 1

Synthesis of EPO-(PEG-DSPE)$_{3.4K}$

420 µg erythropoietin in 300 µl PBS (pH 7.4) is diluted to 900 µl with PBS buffer (pH 6.8). 25 µl of this solution is removed for later analysis by SDS-PAGE. 2.0 mg of (PEG-DSPE)$_{3.4K}$-NHS is dissolved in 2 ml of absolute ethanol and stirred for 30 minutes. 93 µl of the PEG-DSPE$_{3.4K}$-NHS solution is added to 875 µl of the EPO solution. Similar aliquots are added at 40 and 60 minutes into the reaction. The reaction is stirred at ambient temperature for 3 hours. A solution of Tris is added to quench any unreacted reagent.

The reaction mixture is loaded onto a Zorbax GF-250 semi-prep column and eluted with PBS and peaks are collected to give 120 µg of EPO. Mass spectral analysis indicated the molecular weight of the product to be 31,654.44 (calcd. 31,501). SDS PAGE indicated that the major band was ≧99%. Tryptic mapping indicated that the DSPE-PEG was attached to the alpha amino group of amino acid 1.

EXAMPLE 2

Synthesis of EPO-(PEG-linoleate)$_{3.4K}$

Erythropoietin is dissolved in PBS (pH 7.4). To this solution is added a 50% molar excess of (DSPE-linoleate)$_{3.4K}$-NHS dissolved in absolute ethanol. The reaction is stirred at ambient temperature for 3 hours. An aqueous solution of Tris (pH 9.5) is added and the resulting solution stirred for 30 minutes at ambient temperature to quench any unreacted reagent. The reaction mixture is concentrated using a centrifugal concentrator with a membrane cutoff of 5 KD. The concentrated solution is loaded onto a Zorbax GF-250 semi-prep column and eluted with PBS. Peaks are collected and analyzed by SDS PAGE and mass spectrometry. The peak corresponding to EPO-(PEG-linoleate)$_{3.4K}$ is collected and concentrated using a centrifugal concentrator with a membrane cutoff of 5 KD.

EXAMPLE 3

Synthesis of EPO-((PEG-DSPE)$_{3.4K}$)$_2$

Lysyl glycine t-butyl-ester is dissolved in DMF. To this is added a 3 equivalents of PEG-DSPE3.4-K-NHS dissolved in DMF. A drop of the reaction mixture is checked with moist indicator paper and diisopropylethylamine added to the reaction mixture to maintain the pH between 7.5–8.5. The reaction mixture is stirred overnight at ambient temperature. The DMF is removed under reduced pressure and the residue chromatographed to give (DSPE-PEG$_{3.4K}$)$_2$-lysyl glycine t-butyl ester. This material is dissolved in 50% trifluoroacetic acid in methylene chloride and the reaction mixture stirred for one hour at ambient temperature. The solvent is removed under reduced pressure and the residue triturated with diethylether to give (DSPE-PEG$_{3.4K}$)$_2$-lysyl glycine that is used without further purification.

(DSPE-PEG$_{3.4K}$)$_2$-lysyl glycine is dissolved in a minimum amount of DMF along with a 10% molar excess. An equimolar ration of diisopropylcarbodiimide based on (DSPE-PEG$_{3.4K}$)$_2$-lysyl glycine is added and the reaction mixture stirred for 45 minutes. This solution is added dropwise to a solution of erythropoietin in PBS (pH 7.4). The reaction is stirred at ambient temperature for 3 hours. An aqueous solution of Tris (pH 9.5) is added and the resulting solution stirred for 30 minutes at ambient temperature to quench any unreacted reagent. The reaction mixture is concentrated using a centrifugal concentrator with a membrane cutoff of 5 KD. The concentrated solution is loaded onto a Zorbax GF-250 semi-prep column and eluted with PBS. Peaks are collected and analyzed by SDS PAGE and mass spectrometry. The peak corresponding to (DSPE-PEG$_{3.4K}$)$_2$-lysyl glycine-EPO is collected and concentrated using a centrifugal concentrator with a membrane cutoff of 5 KD.

EXAMPLE 4

Synthesis of EPO-PEG$_{3.4K}$-NH—CO—(N-(β-D-galactopyranosyl)-(1→4)-[α-L-fucopyranosyl]-(1→3)-(2-amino-2-deoxy-β-D-glucopyranoside))

To a solution of mono-BOC-diamino-PEG$_{3.4K}$ in THF is added one equivalent of 1,1'-carbonyldiimidazole. The reaction mixture is stirred for one hour at ambient temperature. To this is added a solution of nona-O-acetyl-β-D-galactopyranosyl)-(1→4)-[α-L-fucopyranosyl]-(1→3)-(2-amino-2-deoxy-β-D-glucopyranoside in THF. The reaction mixture is stirred for 4 hours at ambient temperature. The solvent is removed under reduced pressure and the residue dissolved in 50% trifluoroacetic acid in methylene chloride and stirred for 30 minute at ambient temperature. The solvent is removed under reduced pressure and the residue chromatographed to give NH$_2$-PEG$_{3.4K}$-NH—CO—(N-(nona-O-acetyl-(β-D-galactopyranosyl)-(1→4)-[α-L-fucopyranosyl]-(1→3)-(2-amino-2-deoxy-β-D-glucopyranoside))).
This compound is dissolved in THF and one equivalent of bromoacetyl bromide and one equivalent of diisopropylethylamine is added. The reaction mixture is stirred at ambient temperature for one hour. The resulting solution is added dropwise to a solution of Cys-EPO (erythropoietin to which an N-terminal cysteine has been added by recombinant technology). After 4 hours the solution is concentrated and the product purified on a size exclusion column, eluting with PBS. The material corresponding to EPO-PEG$_{3.4K}$-NH—CO—(N-(nona-O-acetyl-(β-D-galactopyranosyl)-(1→4)-[α-L-fucopyranosyl]-(1→3)-(2-amino-2-deoxy-β-D-glucopyranoside))) is collected and aqueous ammonia added to remove the acetyl groups. Further chromatography gives the desired product, EPO-PEG$_{3.4K}$-NH—CO—(N-(β-D-galactopyranosyl)-(1→4)-[α-L-fucopyranosyl]-(1→3)-(2-amino-2-deoxy-β-D-glucopyranoside)).

EXAMPLE 5

Biological Testing

UT7 Cell Proliferation Assay:
Cells were washed three times in PBS and starved for 24 hours prior to assay. UT-7 cells were starved in IMDM with added L-glutamine and FBS at 5% (I5Q). Cells were washed once in 50 mL DPBS and counted while suspended in DPBS and suspended in the appropriate media to a final concentration of 6×10$^5$ cells/mL (yields a final concentration of 30,000 cells per well). An EPO standard was prepared by diluting EPO stock (1.7 mg/mL) to 0.85 µg/mL (2 µL in 4 mL media) This solution was diluted 2:340 to 5 ng/mL followed by 1:2 serial dilutions down to a concentration of 0.0098 ng/mL in I5Q media. This yields standard concentrations of 2.5 ng/mL to 0.0024 ng/mL. EPO-PEG-DSPE was diluted in a similar manner. 50 µL of the UT-7 cell suspension was transferred to the corresponding wells and the plates were incubated at 37° C. for 48 hours. Cell proliferation was assessed using Promega's MTS solution, adding 20 µL per well. Readings were begun 1 hour after MTS addition. The EC50 for EPO was $1.03 \times 10^{-11}$ M and for EPO-PEG-DSPE was $2.22 \times 10^{-11}$ M.

Evaluation of the Efficacy in BDF1 Mice:
BDF1 female mice obtained from Charles Rivers Laboratories (Raleigh, N.C.), weighing approximately 18–20 grams were group housed (10 per cage) in filtered-top plastic cages. The animals were identified with ear tags, placed at least 1 week prior to the start of the study. Cage cards labeled with animal number, test article, treatment, and study number were affixed to the cages.

On Day −5 of the study, the animals were assigned to 1 of 3 treatment groups (PBS control, EPO and EPO-(PEG-DSPE)$_{3.4K}$) with 15 animals in each group. The animals were anesthetized (CO$_2$) and blood samples were taken in EDTA coated glass tube via retro-orbital sinus with a target blood volume of 0.05 mL/sample to establish baseline levels. Blood was placed into commercially available EDTA prepared microcentrifuge tubes. Aliquots were placed into hematocrit tubes and the tubes were sealed with clay and centrifuged for 5 minutes. The Packed Cell Volume (PCV/hematocrit) was obtained from reading the hematocrit tubes on a commercially available hematocrit determinator card. Using 10 µg of blood, hemoglobin levels were determined using a Coulter™ Counter. On Days 0 and 2, the animals received an intraperitoneal injection of 0.94 mL (112.8 mL/kg) of either PBS (pH 7.4), EPO (0.333 µg/mL in PBS), or EPO-(PEG-DSPE)$_{3.4K}$ (0.383 µg/mL in PBS). On days 4, 7 and 10 blood samples taken. Aliquots were placed into hematocrit tubes and the were sealed with clay and centrifuged for 5 minutes. The Packed Cell Volume (PCV/hematocrit) was obtained from reading the hematocrit tubes on a commercially available hematocrit determinator card. Using 10 µl, hemoglobin levels were determined using a Coulter™ Counter.

Results:

|  | Day 0 | Day 4 | Day 7 | Day 10 |
|---|---|---|---|---|
| Hematocrit |  |  |  |  |
| EPO | 44.8 | 48.6 | 50.6 | 45.8 |
| EPO-DSPE | 44.0 | 50.4 | 52.8 | 54.0 |
| PBS | 44.8 | 42.0 | 44.8 | 43.6 |
| Hemoglobin |  |  |  |  |
| EPO | 12.3 | 13.2 | 13.3 | 12.5 |
| EPO-DSPE | 12.2 | 13.5 | 14.2 | 15.0 |
| PBS | 13.0 | 11.9 | 12.4 | 12.7 |

Figure 2:
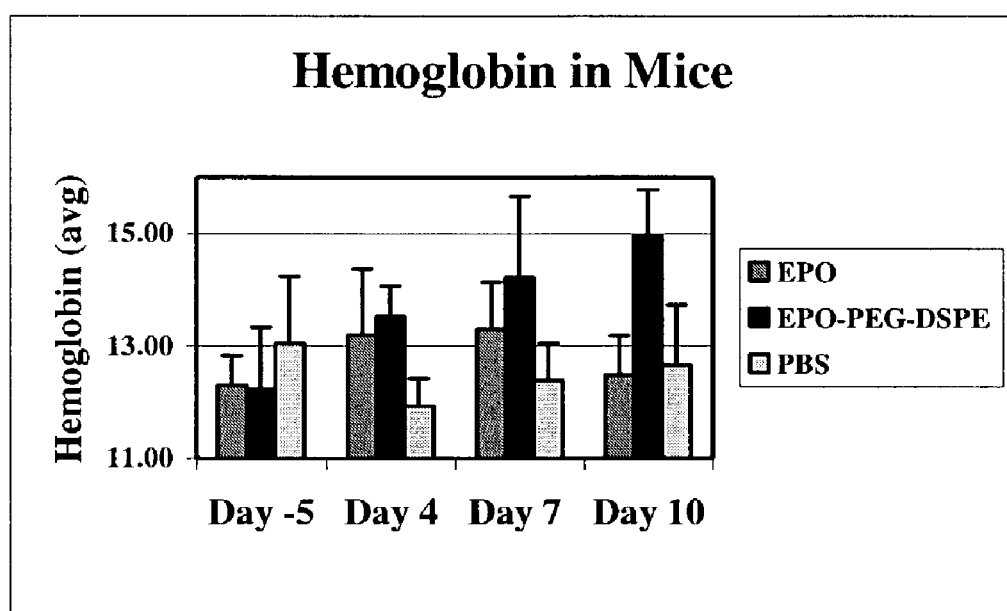
FIG. 2 is a graph showing the hemoglobin levels in mice treated with the composition of the invention versus unmodified EPO and PBS control.

The results are shown graphically in FIGS. 1 and 2.
What is claimed is:

1. A pharmaceutical composition comprising an erythropoietic conjugate having the biological property of causing bone marrow cells to increase production or red blood cells, the conjugate consisting of a compound of the formula EPO-(X-Y)$_n$, wherein EPO is erythropoientin or an erythropoietic moiety, X is a substantially non-antigenic hydrophilic polymer, Y is a phospholipid covalently bonded to said hydrophilic polymer and n is an integer from 1 to 15, and a pharmaceutically acceptable carrier.

2. The pharmaceutical composition of claim 1 wherein the hydrophilic polymer is a polyalkylene oxide.

3. The pharmaceutical composition of claim 2 wherein the polyalkylene oxide is a substituted polyethylene oxide.

4. The pharmaceutical composition of claim 2 wherein the polyalkylene oxide is selected from polyethylene glycol homopolymers, polypropylene glycol homopolymers, alkyl-polyethylene oxides, bispolyethylene oxides and co-polymers thereof, or block co-polymers of polyalkyene oxides.

5. The pharmaceutical composition of claim 2 wherein said polyalkylene oxide is a polyethylene glycol homopolymer having a molecular weight of between about 200 and about 100,000 daltons.

6. The pharmaceutical composition of claim 1 wherein said erythropoietin or erythropoietic moiety is selected from recombinant and non-recombinant mammalian erythropoietin.

7. The pharmaceutical composition of claim 1 wherein said hydrophilic polymer is bonded to the N terminal amino group of the EPO moiety.

8. The pharmaceutical composition of claim 1 comprising one to about four (X-Y) moieties which are each independently covalently bonded to the side chain sulfur atom of a cysteinyl residue of the EPO moiety.

9. The pharmaceutical composition of claim 1 wherein (X-Y) moiety is covalently bonded to the side chain sulfur atom of at least one cysteinyl residue of the EPO moiety.

10. The pharmaceutical composition of claim 1 that causes bone marrow cells to increase production of red blood cells, and has an increased serum half life over unmodified mammalian erythropoietin.

11. The pharmaceutical composition of claim 1 wherein said hydrophilic polymeric group is a linear or branched polyalkane glycol chain, a or a polyvinyl pyrolidone chain, and wherein said hydrophilic polymeric group has a molecular weight of about 800 to about 120,000 Daltons.

12. The pharmaceutical composition of claim 11 wherein said hydrophobic polymeric group is a linear or branched polyalkane glycol chain with a molecular weight greater than 2,000 Daltons.

13. The pharmaceutical composition of claim 12 wherein said hydrophilic polymeric group is a linear or branched polyethylene glycol chain or a linear or branched substituted polyethylene glycol chain or a linear or branched substituted polyethylene glycol chain.

14. The pharmaceutical composition of claim 13 wherein said (X-Y) moiety is a linear or branched polyethylene glycol chain that is terminally substituted with a phospholipid group.

15. The pharmaceutical composition of claim 14 wherein the phospholipid is disteroylphosphatidyl ethanolamine (DSPE).

16. The pharmaceutical composition of claim 14 wherein the hydrophilic polymer-phospholipid moiety is covalently bonded to the N terminus of the EPO moiety.

17. A method of treating anemia comprising administering a therapeutically effective amount of the pharmaceutical composition of claim 1.

18. The method of claim 17 wherein said erythropoietin in the pharmaceutical composition has an increased serum half-life compared to un-conjugated erythropoietin.

* * * * *